(12) United States Patent
Shipley

(10) Patent No.: US 8,273,721 B2
(45) Date of Patent: Sep. 25, 2012

(54) COMBINATION TREATMENT FOR BLADDER CANCER

(75) Inventor: James E. Shipley, Lexington, MA (US)

(73) Assignee: Endo Pharmaceuticals Solutions Inc., Chadds Ford, PA (US)

( * ) Notice: Subject to any disclaimer, the term of this patent is extended or adjusted under 35 U.S.C. 154(b) by 472 days.

(21) Appl. No.: 12/397,831

(22) Filed: Mar. 4, 2009

(65) Prior Publication Data

US 2009/0227529 A1   Sep. 10, 2009

Related U.S. Application Data

(60) Provisional application No. 61/034,003, filed on Mar. 5, 2008.

(51) Int. Cl.
*A61K 31/704* (2006.01)
*C07H 15/252* (2006.01)
(52) U.S. Cl. .......................... 514/34; 536/6.4
(58) Field of Classification Search .................. None
See application file for complete search history.

(56) References Cited

U.S. PATENT DOCUMENTS

| | | | | |
|---|---|---|---|---|
| 2005/0142104 | A1* | 6/2005 | Zeldis | 424/85.1 |
| 2007/0117750 | A1* | 5/2007 | Abdulrazik | 514/12 |
| 2008/0014190 | A1* | 1/2008 | Qian | 424/94.63 |
| 2008/0199452 | A1* | 8/2008 | Gaylis et al. | 424/94.62 |
| 2009/0214634 | A1* | 8/2009 | Chaber et al. | 424/450 |

FOREIGN PATENT DOCUMENTS

RU   2249469 C1   4/2005

OTHER PUBLICATIONS

Friedberg et al., "Automated protein function prediction;the genomic challenge" Briefings in Bioinformatics (2006) vol. 7 No. 3 pp. 225-242.*
Eikenes et al., "Hyaluronidase induces a transcapillary pressure gradient and improves the distribution and uptake of liposomal doxorubicin (Caelyx™) in human osteosarcoma xenografts" British Journal of Cancer (2005) vol. 93 pp. 81-88.*
Kohno et al., "Effects of hyaluronidase on doxorubicin penetration into squamous carcinoma multicellular tumor spheroids and its cell lethality" J Cancer Res Clin Oncol (1994) vol. 120 pp. 293-297.*
Sasaki et al., "Studies on Enhancement of drug absorption through the bladder mucosa" Nippon Hinyokika Gakkai Zasshi (1994) vol. 85 No. 9, pp. 1353-1362.*
Scheithauer et al., "In Vitro Evaluation of the Anticancer Drug Modulatory Effect of Hyaluronidase in Human Gastrointestinal Cell Lines" Anticancer Research (1988) vol. 8 pp. 391-396.*
Database WPI; XP002531524; Thomson Scientific, London, GB; 2005-270897; 1 page.
The Valrubicin Study Group Steinberg et al:"Efficacy and Safety of Valrubicin for the Treatment of Bacillus Calmette-Guerin Refractory Carcinoma in Situ of the Bladder" Journal of Urology, vol. 163, No. 3, Mar. 1, 2000, pp. 761-767.
Schneider T et al: "Nocturia: A non-specific but important symptom of urological disease" International Journal of Urology 200903 AU, vol. 16, No. 3, Mar. 2009, pp. 249-256.
Onrust S V et al: "Valrubicin" Drugs and Aging, ADIS International Ltd, NZ, vol. 15, No. 1, Jan. 1, 1999 , pp. 69-75.
Doehn Christian: "Valrubicin, Anthra Pharmaceuticals Inc" Current Opinion in Oncologic, Endocrine and Metabolic Investigational Drugs, Current Drugs, London, GB, vol. 1, No. 4, Jan. 1, 1999, pp. 407-415.
For the Trospium Study Group Zinner et al: "Trospium Chloride Improves Overactive Bladder Symptoms: A Multicenter Phase III Trial" Journal of Urology, vol. 171, No. 6, Jun. 1, 2004, pp. 2311-2315.
PCT Search Report corresponding to PCT/US2009/036016, dated Jun. 25, 2009; 3 pages.
PCT Written Opinion corresponding to PCT/US2009/036016, dated Jun. 25, 2009; 5 pages.

* cited by examiner

*Primary Examiner* — Eric S Olson
(74) *Attorney, Agent, or Firm* — RatnerPrestia

(57) ABSTRACT

Novel methods useful for treating a patient with bladder cancer such as superficial bladder cancer includes administering to the patient a therapeutically effective amount of valrubicin and trospium chloride.

18 Claims, No Drawings

COMBINATION TREATMENT FOR BLADDER CANCER

CROSS-REFERENCE TO RELATED APPLICATION

This application claims the benefit of U.S. Provisional Application 61/034,003, filed Mar. 5, 2008, the entire contents of which is incorporated herein by reference.

TECHNICAL FIELD

This invention relates in general to the treatment of bladder cancer, and in particular, to compositions and methods for treating patients with superficial bladder cancer using valrubicin and trospium chloride.

BACKGROUND

Bladder cancer is the fourth most common cancer among men and the ninth most common cancer among women. It is estimated that each year in the United States, more than 60,000 people develop bladder cancer, of whom more than 13,000 ultimately die of this disease. Bladder cancer most commonly occur in individuals over 60 years of age. Cigarette smoking, exposure to certain industrially used chemicals such as arylamine derivatives, and diet high in fried meat and fat are strongly associated with the development of bladder cancer.

The urinary bladder is made up of four layers: epithelium, lamina propria, muscularis propria or detrusor muscle, and perivesical soft tissue. The epithelium, also referred as transitional urothelium or epithelium, lines the bladder and is in contact with the urine. Transitional urothelial carcinomas are the most common type of bladder cancer, accounting for more than 90% of all bladder cancer. Clinically, transitional urothelial carcinomas are separated into superficial tumors and muscle invasive tumors. Superficial tumors are those that either do not invade, or those that invade but stay superficial to the deep muscle wall of the bladder. Muscle invasive tumors invade the detrusor muscle (pathologic stages pT2-pT4) and are highly aggressive. When bladder cancer invades the muscular layers of the bladder wall it may spread by way of the lymph and blood systems to invade bone, liver, and lungs.

The treatment of muscle invasive tumors requires cystectomy, a surgical procedure that removes all or part of the urinary bladder. Superficial bladder cancer can be treated without cystectomy, usually by transurethral resection (TUR) with or without adjuvant intravesical chemotherapy or immunotherapy. Superficial bladder cancer include noninvasive papillary carcinoma, superficial invasive carcinoma, and carcinoma in situ (CIS). Carcinoma in situ of the urinary bladder is a highly malignant and aggressive cancerous lesion.

Patients with carcinoma in situ of the urinary bladder are usually treated with transurethral resection or fulguration followed by adjuvant intravesical chemotherapy or immunotherapy. Adjuvant chemotherapy or immunotherapy followed by transurethral resection may reduce the rate of recurrence of bladder cancer and increase the overall survival rate. Currently, Bacille Calmette-Guerin (BCG) is the commonly used immunotherapeutic agent, and Mitomycin C the chemotherapeutic agent in conjunction with transurethral resection. It has been shown however that the efficacy of BCG and Mitomycin C is limited and some patients are refractory to BCG or Mitomycin C intravesical treatment.

VALSTAR® (Indevus Pharmaceuticals, Inc., Lexington, Mass.) is currently the only drug approved by the U.S. Food and Drug Administration (FDA) for therapy of BCG-refractory carcinoma in situ of bladder cancer, and has been used for treating patients who are not candidates for cystectomy. VALSTAR® is a sterile solution for intravesical instillation of valrubicin, which is a chemotherapeutic anthracycline derivative.

Clinical studies showed that many patients who received intravesical VALSTAR® treatment experienced local adverse events during or shortly after instillation of VALSTAR®, and within 1 to 7 days after the instillate is removed from the bladder. In a study among 170 patients who received 800 mg dose of VALSTAR® in a multiple-cycle treatment regimen, approximately 28 percent of the patients experienced bladder spasm and 22 percent experienced bladder pain. Bladder spasm is undesirable since it leads to leakage of the medicine and reduce the efficacy of the treatment. Therefore, further developments are needed in the treatment of bladder cancer, especially superficial bladder cancer.

SUMMARY

The invention is directed to novel methods useful in treating patients suffering from bladder cancer such as superficial bladder cancer. The methods comprise administering to the patient a therapeutically effective amount of valrubicin and trospium chloride.

Valrubicin and trospium chloride may be administered concomitantly, or sequentially. Valrubicin and trospium chloride may be administered parenterally.

In some embodiments, valrubicin is administered parenterally, and trospium chloride is administered enterally.

In some embodiments, valrubicin and trospium chloride are co-administered in a combined dosage.

In a preferred embodiment, the method further comprises the step of performing a transurethral resection procedure on the patient prior to administering valrubicin and trospium chloride.

In another aspect, the invention is directed to a pharmaceutical composition useful in treating a patient suffering from superficial bladder cancer. The pharmaceutical composition comprises a therapeutically effective amount of valrubicin or its pharmaceutically acceptable salt, trospium chloride, and optionally a pharmaceutically acceptable carrier.

In a preferred embodiment, the pharmaceutical composition comprises about 5 to 100 mg/mL valrubicin or its pharmaceutically acceptable salt, and about 5 to 100 mg/mL trospium chloride.

DETAILED DESCRIPTION OF PREFERRED EMBODIMENTS

Various embodiments of the invention are described hereinafter. It should be noted that the specific embodiments are not intended as an exhaustive description of the invention or as a limitation on the scope of the invention. One aspect described in conjunction with a particular embodiment of the present invention is not necessarily limited to that embodiment and can be practiced with any other embodiment(s) of the invention.

In general, the present invention is directed to a pharmaceutical composition useful in treating a patient with superficial bladder cancer. The pharmaceutical composition comprises an effective amount of valrubicin and trospium chloride and optionally pharmaceutically acceptable carrier. The present invention is further directed to a method of treating patients suffering from superficial bladder cancer. The method generally comprises administering to a patient with superficial bladder cancer an effective amount of valrubicin and trospium chloride.

In some embodiments, the provided pharmaceutical composition and the method of treating patients with superficial bladder cancer are used in conjunction with a transurethral resection procedure. Procedure of performing transurethral resection is known to those skilled in the art, and thus it is not described in great detail in order to simplify the description of the invention. Briefly, in a transurethral resection procedure, a cystoscopy, a thin lighted tube with a lens, is inserted into the bladder through the urethra to view the cancerous area. A tool with a small wire loop on an end is then used to remove the cancer or to burn the tumor away with high-energy electricity. A therapeutically effective amount of valrubicin and trospium chloride are administered to the patient, either sequentially or concomitantly, after the transurethral resection procedure.

Valrubicin is N-trifluoroacetyladriamycin-14-valerate. The chemical name of valrubicin is (2S-cis)-2-[1,2,3,4,6,11-hexahydro-2,5,12-trihydroxy-7-methoxy-6,11-dioxo-4-[[2,3,6-trideoxy-3-[(trifluoroacetyl)amino]-α-L-lyxo-hexopyranosyl]oxyl]-2-naphthacenyl]-2-oxoethyl pentanoate. The chemical structure of valrubicin is shown below:

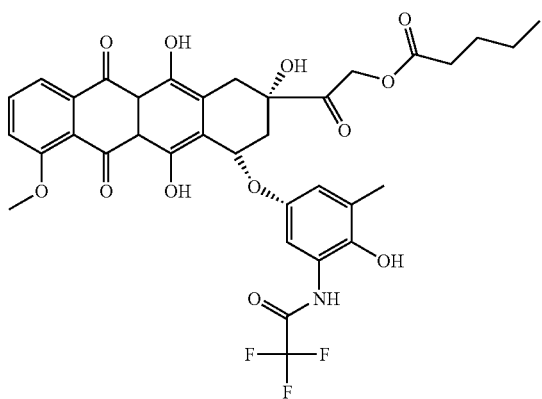

Valrubicin is a known cytotoxic agent. It is an orange or orange-red powder having a molecular weight of 723.65. Valrubicin is highly lipophilic, soluble in methylene chloride, ethanol, methanol and acetone and relatively insoluble in water.

Valrubicin is commercially available from Indevus Pharmaceuticals, Inc., Lexington, Mass. By way of example, VALSTAR® available from Indevus Pharmaceuticals, Inc. is a FDA approved drug used for the therapy of BCG-refractory carcinoma in situ of the urinary bladder. VALSTAR® is a sterile solution for intravesical instillation of valrubicin. Each vial of VALSTAR® contains valrubicin at a concentration of 40 mg/mL in 50% CREMOPHOR®EL (polyoxyethyleneglycol triricinoleate) and 50% dehydrated alcohol without preservatives or other additives.

Valrubicin is administered to a patient with bladder cancer in a therapeutically effective amount to kill or damage cancerous cells. Depending on the severity of bladder cancer, valrubicin may be administered in an amount ranging from about 200 mg to about 1000 mg once a week over a course of two to eight weeks. The therapeutically effective amount can be readily determined by the attending doctor, as one skilled in the art, by the use of known techniques and by observing results obtained under analogous circumstances. In determining the therapeutically effective amount or dose, a number of factors are considered by the attending doctor, including, but not limited to: the size, age, and general health of the patient; the degree or severity of the disease; the response of the individual patient; the mode of administration; the bioavailability characteristics of the preparation administered; the dose regimen selected; the use of concomitant medication; and other relevant circumstances.

Valrubicin may be administered by any pharmaceutically acceptable means and in any pharmaceutically acceptable carrier. As used herein, "pharmaceutically acceptable carrier" includes any and all solvents, dispersion media, antibacterial and antifungal agents, isotonic agents, absorption delaying agents, and the like. The use of such media and agents for pharmaceutically active substances is well known in the art.

By way of example, valrubicin may be parenterally administered in form of liquid. The liquid includes therapeutic valrubicin and a pharmaceutically acceptable carrier such as polyoxyethyleneglycol triricinoleate and dehydrated alcohol. For example, a dose such as 800 mg valrubicin may be administered intravesically once a week for six weeks. The intravesical administration may begin two weeks after transurethral resection and/or fulguration. Alternatively, the intravesical administration may begin within two weeks of transurethral resection and/or fulguration. Intravesical instillation of valrubicin may be carried out by means known to the ordinary skill in the art. For example, a urethral catheter may be inserted into the patient's bladder to drain the bladder. The liquid containing valrubicin is instilled slowly such as via gravity flow over a period of several minutes. The catheter is then withdrawn. The valrubicin is retained in the patient for a period of time such as two hours before being disposed.

In some preferred embodiments, valrubicin is administered sequentially or concomitantly with trospium chloride. Trospium chloride is spiro[8-azoniabicyclo[3,2,1]octane-8,1'pyrrolidinium]-3-[(hydroxydiphenyl-acetyl)-oxy]chloride (1α, 3β, 5α)(9Cl). Trospium chloride is a quaternary ammonium compound having the following chemical structure:

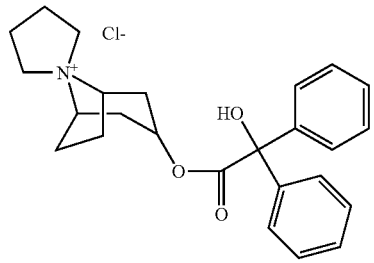

Trospium chloride is a fine, colorless to slightly yellow, crystalline solid having a molecular weight of 427.97. The solubility of trospium chloride in water is approximately 1 g/2 mL.

Trospium chloride is commercial available. By way of example, SANCTURA® tablet available from Indevus Pharmaceuticals, Inc. contains 20 mg trospium chloride. Other inactive ingredients contained in SANCTURA® tablet include sucrose, wheat starch, microcrystalline cellulose, talc, lactose, monohydrate, calcium carbonate, titanium dioxide, stearic acid, croscarmellose sodium, povidone, polyethylene glycol 8000, colloidal silicon dioxide, ferric oxide, carboxymethylcellulose sodium, white wax, magnesium stearate, and carnauba wax.

Trospium chloride is an antispasmodic, antimuscarinic agent. Trospium chloride antagonizes the effect of acetylcholine on muscarinic receptors in cholinergically innervated organs. Its parasympatholytic action reduces the tonus of smooth muscle in the bladder, thus decreasing bladder contractions. Clinical studies have showed that patients who received intravesical treatment with chemotherapeutic or immunotherapeutic agents such as VALSTAR® experienced bladder spasm and bladder pain. Bladder spasm is undesirable as it causes leakage of chemotherapeutic or immunotherapeutic agents, thus reducing the efficacy of the treatment. Trospium chloride can reduce or eliminate bladder spasm and bladder pain. Therefore, administration of trospium chloride can advantageously mitigate or eliminate the leakage of the medicines, and thus increasing the efficacy of the intravesical treatment.

Trospium chloride may be administered to a patient with bladder cancer sequentially or concomitantly with valrubicin. Depending on the severity of bladder spasm, trospium chloride may be administered in an amount ranging from about 10 mg to about 40 mg twice daily. The therapeutically effective amount can be readily determined by the attending doctor, as one skilled in the art, by considering factors including, but not limited to: the size, age, and general health of the patient; the degree or severity of the bladder spasm; the response of the individual patient; the mode of administration; the bioavailability characteristics of the preparation administered; the dose regimen selected; the use of concomitant medication; and other relevant circumstances.

Trospium chloride may be administered by any pharmaceutically acceptable means and in any pharmaceutically acceptable form. For example, trospium chloride may be administered orally in the form of either liquid or solid. Trospium chloride may be in form of solution, suspension, tablet, capsule, oral quick dissolve, sachet or sprinkle. For oral administration, trospium chloride is preferably combined with one or more pharmaceutically acceptable excipients, fillers and/or diluents. Tablets or pills may be coated by conventional techniques to control disintegration and absorption of trientine in the gastrointestinal tract.

Trospium chloride may also be administered parenterally (e.g., intravenously, intramuscularly or subcutaneously). For parenteral administration, trospium chloride is dissolved in a suitable solvent, forming a solution which may be injected. In a preferred embodiment, trospium chloride is administered with valrubicin in a combined dosage form. Valrubicin and trospium chloride may be dissolved in a suitable solvent, forming a suspension or solution. As such, the combined dosage form may be instilled into the bladder (i.e., intravesicle administration). Alternatively, trospium chloride may be administered as a tablet or pill followed by instillation of a valrubicin solution.

In one aspect, a pharmaceutical composition is provided comprising an effective amount of valrubicin or its pharmaceutically acceptable salt and an effective amount of trospium chloride and optionally one or more pharmaceutically acceptable carriers and/or excipients. The pharmaceutical composition may be in any suitable liquid form such as solution or suspension. The pharmaceutical composition may be used for treating patients suffering from superficial bladder cancer. The pharmaceutical composition may be administered to the patient's bladder in conjunction with a transurethral resection procedure.

By way of example, the pharmaceutical composition may comprise about 5 to 100 mg/mL valrubicin, and about 5 to 100 mg/mL trospium chloride. In a preferred embodiment, the pharmaceutical composition may comprise about 5 to 100 mg/mL valrubicin, and about 5 to 100 mg/mL trospium chloride in 50 Vol. % Cremophor EL and 50 Vol. % dehydrated alcohol.

By way of example, the following formulations may be used in conjunction with the method of the invention in treatment of bladder cancer.

Example 1

Valrubicin Formulations Containing DMSO as Permeation Enhancer

|  |  | Formulation | | | | |
| --- | --- | --- | --- | --- | --- | --- |
| Compound | Valstar ® | 1 | 2 | 3 | 4 | 5 |
| Valrubicin | 200 mg | 200 mg | 200 mg | 200 mg | 200 mg | 200 mg |
| Cremophor | 2.5 ml | 2.5 ml | 2.5 ml | — | — | — |
| Ethanol | 2.5 ml | 2.5 ml | — | — | — | — |
| DMSO | — | 2.5 ml | 2.5 ml | 5.0 ml | 5.0 ml | — |
| Reconstitution Medium | 50 ml Saline | 50 ml Saline | 50 mL Saline | 50 ml Saline | 25 ml DMSO 25 ml Saline | 55 ml DMSO |

Example 2

Valrubicin Formulations Containing DMSO and Mucin Degrading Enzyme

|  | Formulation | | | |
| --- | --- | --- | --- | --- |
| Compound | 1 | 2 | 3 | 4 |
| Valrubicin | 200 mg | 200 mg | 200 mg | 200 mg |
| Cremophor | 2.5 ml | 2.5 ml | 2.5 ml | 2.5 ml |
| Ethanol | — | — | — | — |
| DMSO | 2.5 ml | 2.5 ml | 2.5 ml | 2.5 ml |
| Pretreatment Enzyme | Trypsin | Animal Hyaluronidase | Human Recombinant Hyaluronidase | — |
| Co-delivered Enzyme | — | — | — | Trypsin |
| Reconstitution Medium | 50 ml Saline | 50 ml Saline | 50 ml Saline | 50 ml Saline |

Example 3

Valrubicin Formulations Containing DMSO and Mucoadhesive Agents

| | Formulation | | | |
|---|---|---|---|---|
| Compound | 1 | 2 | 3 | 4 |
| Valrubicin | 200 mg | 200 mg | 200 mg | 200 mg |
| Cremophor | 2.5 ml | 2.5 ml | 2.5 ml | 2.5 ml |
| Ethanol | — | — | — | — |
| DMSO | 2.5 ml | 2.5 ml | 2.5 ml | 2.5 ml |
| Mucoadhesive Agent* | Polyacrylic Acid | Carboxy-methylcellulose | Hyaluronic Acid | — |
| Reconstitution Medium | 50 ml Saline | 50 ml Saline | 50 ml Saline | 50 ml Saline 3% HA |

*3% of Total Solution

Example 4

Valrubicin Formulations Containing DMSO and a Tight Junction Modifier (TJM)

| | Formulation | | | |
|---|---|---|---|---|
| Compound | 1 | 2 | 3 | 4 |
| Valrubicin | 200 mg | 200 mg | 200 mg | 200 mg |
| Cremophor | 2.5 ml | 2.5 ml | — | — |
| DMSO | 2.5 ml | 2.5 ml | — | — |
| TJM* | Trimethyl Chitosan | Monocarboxy-methyl-chitosan | Trimethyl Chitosan | Trimethyl Chitosan |
| Reconstitution Medium | 50 ml Saline | 50 ml Saline | 25 ml Saline 25 ml DMSO | 50 ml DMSO |

*1% to 5% of Total Solution

Example 5

Liposomal Formulations of Valrubicin

| | Liposomal Formulation Mole Ratio (Ranges) | | | | | | | | | | |
|---|---|---|---|---|---|---|---|---|---|---|---|
| Component | 1 | 2 | 3 | 4 | 5 | 6 | 7 | 8 | 9 | 10 | 11 |
| Valrubicin | 1-2 | 1-2 | 1-2 | 1-2 | 1-2 | 1-2 | 1-2 | 1-2 | 1-2 | 1-2 | 1-2 |
| Phosphatidyl Choline | — | — | — | 4-7 | 4-7 | 4-7 | 4-7 | 4-7 | 4-7 | 4-7 | 4-7 |
| Cholesterol | — | 1-2 | — | 1-2 | 1-2 | 1-2 | 1-2 | 1-2 | 1-2 | 1-2 | 1-2 |
| Oleic acid | 1-2 | — | 1-2 | — | — | — | — | — | — | — | — |
| Phosphatidyl Ethanolamine | 4-7 | 2-6 | 2-6 | — | — | — | — | — | — | — | — |
| Phosphatidyl inositol | 2-4 | 2-4 | 1-2 | — | — | — | — | — | — | — | — |
| Diglyceride succinate | — | — | 3-4 | — | — | — | — | — | — | — | — |
| D-glucosyl-β1-1'Ceramide (C8) | — | — | — | 2-4 | — | — | — | — | — | — | — |
| D-glucosyl-β1-1'Ceramide (C12) | — | — | — | — | 2-4 | — | — | — | — | — | — |
| D-glucosyl-β1, 1'N-palmitoyl-D-erythro-sphinosine | — | — | — | — | — | 2-4 | — | — | — | — | — |
| D-galactosyl-β1-1'Ceramide (C8) | — | — | — | — | — | — | 2-4 | — | — | — | — |
| D-galactosyl-β1-1'Ceramide (12) | — | — | — | — | — | — | — | 2-4 | — | — | — |
| D-galactosyl-β1-1'-N-Nervonyl-D-erythro-sphingosine | — | — | — | — | — | — | — | — | 2-4 | — | — |
| D-glactose-β1-1'Ceramide (C8) | — | — | — | — | — | — | — | — | — | 2-4 | — |
| D-glactose-β1-1'Ceramide (C12) | — | — | — | — | — | — | — | — | — | — | 2-4 |
| Suspending medium: | Pharmaceutically acceptable isotonic solution with or without any buffering capacity. | | | | | | | | | | |

Example 6

Selected Formulations

| Compound | Formulation | | | | | |
|---|---|---|---|---|---|---|
| | 1 | 2 | 3 | 4 | 5 | 6 |
| Valrubicin | 800 mg | 800 mg | 800 mg | 800 mg | — | 800 mg |
| Cremophor | 10 ml | 10 ml | 10 ml | 10 ml | 10 ml (1) | — |
| DMSO | 10 ml | 10 ml | 10 ml | 10 ml | 10 ml | — |
| GAG Remover | Trypsin | Trypsin | Trypsin | — | Trypsin | — |
| Mucoadhesive TJM | — | PAA (4) | PAA Carbopol 934P | PAA Carbopol 934P | Carbopol 934P | Carbopol 934P |
| Cyclodextrin | — | — | — | — | — | Hydroxy-propyl-β-Cyclodextrin (3) |
| Val/PVP Co-precipitate 800/8000$^2$ | — | — | — | — | 88 g | — |
| Reconstitution Medium | Saline | Saline | Saline | Saline | Saline | Saline |

1. Only if needed
$^2$Co-precipitate prior to use
3. 5 to 8 grams
4. Polyacrylic acid The pharmaceutical composition may be administered in any pharmaceutically acceptable means. The pharmaceutical composition can be administered to a patient with superficial bladder cancer in conjunction with transurethral resection procedure. For example, the pharmaceutical composition may be parenterally administered once a week for six weeks. The intravesical administration may begin two weeks after transurethral resection and/or fulguration. Alternatively, the intravesical administration may begin within two weeks after transurethral resection and/or fulguration. Intravesical instillation of valrubicin may be carried out by means known to the ordinary skill in the art. For example, a urethral catheter may be inserted into the patient's bladder to drain the bladder. The liquid containing valrubicin is instilled slowly such as via gravity flow over a period of several minutes. The catheter is then withdrawn. The valrubicin is retained in the patient for a period of time such as two hours before disposed.

From the foregoing it will be appreciated that, although specific embodiments of the invention have been described herein for purposes of illustration, various modifications may be made without deviating from the spirit and scope of the invention claimed in the claims.

What is claimed is:

1. A method of treating a patient suffering from bladder cancer comprising administering to the patient a therapeutically effective amount of valrubicin, trospium chloride, and a mucin degrading enzyme comprising trypsin or hyaluronidase.

2. The method of claim 1 in which said administration of valrubicin and trospium chloride is carried out concomitantly.

3. The method of claim 1 in which said administration of valrubicin and trospium chloride is carried out sequentially.

4. The method of claim 1 in which said administration of valrubicin and trospium chloride is carried out parenterally.

5. The method of claim 1 in which said administration of valrubicin is carried out parenterally.

6. The method of claim 1 in which said administration of trospium chloride is carried out enterally.

7. The method of claim 1 in which said administration of valrubicin is carried out parenterally, and said administration of trospium chloride is carried out enterally.

8. The method of claim 1 in which said valrubicin and trospium chloride are co-administered in a combined dosage form comprising about 5 to 100 mg/mL valrubicin, and about 5 to 100 mg/mL trospium chloride.

9. The method of claim 1 further comprising the step of performing a transurethral resection procedure on the patient prior to the administration step.

10. The method of claim 1 in which said administration step is carried out to a patient suffering from superficial bladder cancer.

11. The method of claim 1 in which said administration step is carried out to a patient suffering from carcinoma in situ of urinary bladder.

12. A pharmaceutical composition comprising a therapeutically effective amount of valrubicin or its pharmaceutically acceptable salt, trospium chloride, a mucin degrading enzyme comprising trypsin or hyaluronidase, and optionally a pharmaceutically acceptable carrier.

13. The pharmaceutical composition of claim 12 which comprising about 5 to 100 mg/mL valrubicin or its pharmaceutically acceptable salt, and about 5 to 100 mg/mL trospium chloride.

14. The method of claim 1, wherein the mucin degrading enzyme comprises trypsin, animal hyaluronidase, or human recombinant hyaluronidase.

15. The method of claim 1, wherein the mucin degrading enzyme comprises trypsin.

16. The pharmaceutical composition of claim 12, wherein the mucin degrading enzyme comprises trypsin, animal hyaluronidase, or human recombinant hyaluronidase.

17. The new pharmaceutical composition of claim 12, wherein the mucin degrading enzyme comprises trypsin.

18. The pharmaceutical composition of claim 12, wherein the pharmaceutically acceptable carrier comprises saline.

* * * * *

UNITED STATES PATENT AND TRADEMARK OFFICE
CERTIFICATE OF CORRECTION

| | | |
|---|---|---|
| PATENT NO. | : 8,273,721 B2 | |
| APPLICATION NO. | : 12/397831 | |
| DATED | : September 25, 2012 | |
| INVENTOR(S) | : James E. Shipley | |

It is certified that error appears in the above-identified patent and that said Letters Patent is hereby corrected as shown below:

At Column 10, line 61, Claim 17 should read

-- The pharmaceutical composition of claim 12, wherein the mucin degrading enzyme comprises trypsin. --

Signed and Sealed this
First Day of January, 2013

David J. Kappos
*Director of the United States Patent and Trademark Office*